(12) United States Patent
Sugiura et al.

(10) Patent No.: US 12,178,408 B2
(45) Date of Patent: Dec. 31, 2024

(54) ENDOSCOPE

(71) Applicant: FUJIFILM Corporation, Tokyo (JP)

(72) Inventors: Naoki Sugiura, Kanagawa (JP);
Toshihiko Izaki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/047,279

(22) Filed: Oct. 18, 2022

(65) Prior Publication Data
US 2023/0055128 A1 Feb. 23, 2023

Related U.S. Application Data

(62) Division of application No. 16/118,469, filed on Aug. 31, 2018, now Pat. No. 11,503,983.

(30) Foreign Application Priority Data

Sep. 28, 2017 (JP) .................................. 2017-188595

(51) Int. Cl.
*A61B 1/12* (2006.01)
*A61B 1/00* (2006.01)
(Continued)

(52) U.S. Cl.
CPC ............ *A61B 1/126* (2013.01); *A61B 1/0008* (2013.01); *A61B 1/00091* (2013.01);
(Continued)

(58) Field of Classification Search
CPC .............. A61B 1/00091; A61B 1/0008; A61B 1/00094; A61B 1/12; A61B 1/126;
(Continued)

(56) References Cited

U.S. PATENT DOCUMENTS 5,518,502 A * 5/1996 Kaplan .................. A61B 1/127
600/156
5,630,795 A * 5/1997 Kuramoto .......... A61B 1/00137
604/35

(Continued)

FOREIGN PATENT DOCUMENTS

CN 1638685 7/2005
CN 2774381 4/2006
(Continued)

OTHER PUBLICATIONS

"Search Report of Europe Counterpart Application", issued on Feb. 18, 2019, p. 1-p. 8.
(Continued)

*Primary Examiner* — Ryan N Henderson
(74) *Attorney, Agent, or Firm* — JCIPRNET

(57) ABSTRACT

An endoscope includes a distal end surface provided at a distal end of an insertion part; an observation window provided on the distal end surface; a fluid jetting nozzle; and a first protective projection, a second protective projection, and a third protective projection disposed at an outer peripheral part of the distal end surface and provided to project forward of the observation window. In all combinations of imaginary planes capable of coming into contact with the first protective projection, the second protective projection, and the third protective projection from a front side, the imaginary planes are disposed forward of the observation window, the imaginary planes are disposed at the same height as or forward of the fluid jetting nozzle, and the observation window and a portion of the fluid jetting nozzle are included within an outer ring region surrounded by the first protective projection, the second protective projection, and the third protective projection.

5 Claims, 10 Drawing Sheets

(51) Int. Cl.
*A61B 1/015* (2006.01)
*A61B 1/05* (2006.01)

(52) U.S. Cl.
CPC .......... *A61B 1/00096* (2013.01); *A61B 1/015* (2013.01); *A61B 1/00119* (2013.01); *A61B 1/00174* (2013.01); *A61B 1/05* (2013.01)

(58) Field of Classification Search
CPC ..... A61B 1/127; A61B 1/015; A61B 1/00096; A61B 1/00174; A61B 1/05; A61B 1/00119
See application file for complete search history.

(56) References Cited

U.S. PATENT DOCUMENTS

| | | | | |
|---|---|---|---|---|
| 6,358,199 | B1* | 3/2002 | Pauker | A61B 1/00133 600/102 |
| 7,896,802 | B2* | 3/2011 | Otawara | A61B 1/00091 600/176 |
| 7,936,369 | B2 | 5/2011 | Takase et al. | |
| 8,033,990 | B2* | 10/2011 | Otawara | A61B 1/05 600/129 |
| 8,092,375 | B2* | 1/2012 | Otawara | A61B 1/00091 600/176 |
| 8,394,013 | B2* | 3/2013 | Ichimura | A61B 1/00188 600/129 |
| 8,419,631 | B2* | 4/2013 | Kase | A61B 1/0625 600/129 |
| 8,740,779 | B2* | 6/2014 | Yoshida | A61B 1/0638 600/177 |
| 8,777,845 | B2* | 7/2014 | Ikeda | A61B 1/12 600/129 |
| 9,173,555 | B2* | 11/2015 | Ikeda | A61B 1/12 |
| 9,282,882 | B2* | 3/2016 | Ikeda | A61B 1/12 |
| 9,521,948 | B2 | 12/2016 | Ikeda et al. | |
| 9,943,217 | B2* | 4/2018 | Ikeda | A61B 1/00091 |
| 10,441,151 | B2 | 10/2019 | Ikeda et al. | |
| 10,779,717 | B2* | 9/2020 | Kuwae | A61B 1/00091 |
| 2004/0267092 | A1* | 12/2004 | Ishibiki | A61B 1/00089 600/127 |
| 2006/0041245 | A1* | 2/2006 | Ferry | A61B 17/3403 604/95.01 |
| 2006/0161043 | A1* | 7/2006 | Neumann | A61B 1/00133 600/101 |
| 2006/0161047 | A1* | 7/2006 | Miyoshi | A61B 1/00091 600/173 |
| 2006/0229497 | A1* | 10/2006 | Toyama | A61B 1/07 600/156 |
| 2006/0244821 | A1 | 11/2006 | Takase et al. | |
| 2007/0027360 | A1* | 2/2007 | Mitsuya | A61B 1/00071 600/141 |
| 2007/0260118 | A1* | 11/2007 | Otawara | A61B 1/0008 600/176 |
| 2008/0064928 | A1* | 3/2008 | Otawara | A61B 1/051 600/129 |
| 2008/0086032 | A1* | 4/2008 | Ichimura | A61B 1/05 600/156 |
| 2009/0093681 | A1* | 4/2009 | Ichimura | A61B 1/00096 600/178 |
| 2009/0253966 | A1* | 10/2009 | Ichimura | A61B 1/00181 600/158 |
| 2011/0112363 | A1* | 5/2011 | Koga | A61B 1/126 600/109 |
| 2012/0226104 | A1* | 9/2012 | Ikeda | A61B 1/126 600/129 |
| 2013/0172680 | A1 | 7/2013 | Polyakov et al. | |
| 2013/0274657 | A1* | 10/2013 | Zirps | A61M 25/0147 604/95.01 |
| 2014/0094659 | A1* | 4/2014 | Hamazaki | G02B 23/2476 600/157 |
| 2016/0015258 | A1 | 1/2016 | Levin et al. | |
| 2016/0051130 | A1 | 2/2016 | Mitsuya | |
| 2016/0174824 | A1* | 6/2016 | Ikeda | A61B 1/00163 600/104 |
| 2016/0309994 | A1* | 10/2016 | Kuwae | A61B 1/12 |
| 2019/0254508 | A1 | 8/2019 | Levin et al. | |
| 2020/0000330 | A1 | 1/2020 | Ikeda et al. | |
| 2022/0087517 | A1 | 3/2022 | Levin et al. | |

FOREIGN PATENT DOCUMENTS

| | | |
|---|---|---|
| CN | 101156767 | 4/2008 |
| CN | 101170941 | 4/2008 |
| CN | 102648841 | 8/2012 |
| CN | 102652663 | 9/2012 |
| CN | 106063697 | 11/2016 |
| CN | 106659368 | 5/2017 |
| EP | 2491848 | 8/2012 |
| EP | 2494909 | 9/2012 |
| EP | 3092940 | 11/2016 |
| JP | S58160001 | 10/1983 |
| JP | S62192701 | 12/1987 |
| JP | H0255310 | 2/1990 |
| JP | H10192225 | 7/1998 |
| JP | 2003245244 | 9/2003 |
| JP | 2005052359 | 3/2005 |
| JP | 2005192638 | 7/2005 |
| JP | 2012179078 | 9/2012 |
| JP | 2012179221 | 9/2012 |
| JP | 2015119756 | 7/2015 |
| WO | 2006073122 | 7/2006 |
| WO | 2015072330 | 5/2015 |

OTHER PUBLICATIONS

"Office Action of Japan Counterpart Application", issued on Sep. 11, 2020, with English translation thereof, p. 1-p. 7.
"Office Action of Japan Counterpart Application", issued on Nov. 17, 2020, with English translation thereof, p. 1-p. 5.
"Office Action of China Counterpart Application", issued on Feb. 13, 2023, with English translation thereof, p. 1-p. 15.

* cited by examiner

ENDOSCOPE

CROSS-REFERENCE TO RELATED APPLICATIONS

This application is a divisional application of and claims the priority benefit of a prior application Ser. No. 16/118,469, filed on Aug. 31, 2018. The prior application Ser. No. 16/118,469 claims priority under 35 U.S.C. § 119 to Japanese Patent Application No. 2017-188595, filed on Sep. 28, 2017. Each of the above application(s) is hereby expressly incorporated by reference, in its entirety, into the present application.

BACKGROUND OF THE INVENTION

1. Field of the Invention

The present invention relates to an endoscope, and particularly, to an endoscope for improving protection of an observation window in a distal end part of an insertion part.

2. Description of the Related Art

In a distal end part of an insertion part of an endoscope, an observation window that takes in subject light from an area to be observed, and an illumination window that emits illumination light to the area to be observed are disposed on a distal end surface. Additionally, in order to remove adhering substances, such as a body fluid adhering to the observation window, a fluid jetting nozzle (air/water supply nozzle), which jets a fluid, such as a cleaning liquid (water or the like) or gas (air or the like), toward the observation window, is disposed in the distal end surface.

In a case where the distal end surface of the endoscope comes into contact with a top plate of a workbench at the time of preparatory work, a floor surface at the time of being gripped by an operator at the time of examination, a floor surface at the time of being hung on a hanger, baths of a sink and a washer at the time of cleaning and disinfection, or the like (hereinafter referred to as a "contacted member"), there is a concern that the observation window and the illumination window may be damaged by coming into contact with the contacted member. Particularly, in a case where the observation window (objective lens) has a convex shape, a possibility of contact of the observation window becomes high.

As an endoscope that prevents contact of a lens portion of the observation window and improves impact resistance, for example, the following JP2005-192638A discloses an endoscope in which a first contact distal end part provided in an air/water supply nozzle and a second contact distal end part provided except for at least one of the observation window or illumination means are formed.

SUMMARY OF THE INVENTION

However, the endoscope described in JP2005-192638A is adapted such that the first contact distal end part and the second contact distal end part prevent the endoscope from contacting with the contacted member. However, in a case where the first contact distal end part and the second contact distal end part are laterally shifted from a straight line connecting these contact end parts, there is a case where a contacted member, such as a top surface or a floor, may come into contact with the observation window.

Additionally, since the first contact distal end part is provided in the air/water supply nozzle, it is also considered that the air/water supply nozzle is damaged by coming into contact with the contacted member.

The invention has been made in view of such circumstances, and an object thereof is to provide an endoscope that can prevent an observation window from being contacted from all directions and can reduce impact resulting from contact with a fluid jetting nozzle.

In order to achieve the object of the invention, an endoscope related to the invention comprises an insertion part to be inserted into a subject; a distal end surface provided at a distal end of the insertion part; an observation window provided on the distal end surface to observe an interior of the subject; a nozzle provided on the distal end surface to jet a fluid toward the observation window; and a plurality of protective projections disposed at an outer peripheral part of the distal end surface and provided to project forward of the observation window. In all combinations of imaginary planes capable of coming into contact with the plurality of protective projections from a front side, the imaginary planes are disposed forward of the observation window, the imaginary planes are disposed at the same height as the nozzle or forward of the nozzle, and the observation window and at least a portion of the nozzle are included within an outer ring region surrounded by the plurality of protective projections, in plan view of the distal end surface.

In the one aspect of the invention, it is preferable that the distal end surface has a first surface on which the nozzle is disposed and a second surface which is provided at a projecting part projecting forward from the first surface and on which the observation window is disposed.

In the one aspect of the invention, it is preferable that the plurality of protective projections include a first protective projection provided on the second surface, and the first protective projection is disposed at a position offset to one side of an imaginary straight line connecting a center of the nozzle and a center of the observation window together.

In the one aspect of the invention, it is preferable that the distal end surface has a fluid discharge surface that is provided on a side opposite to the nozzle with respect to the observation window and is inclined rearward as a distance from the observation window increases.

In the one aspect of the invention, it is preferable that the first protective projection is provided at a position adjacent to the fluid discharge surface.

In the one aspect of the invention, it is preferable that the plurality of protective projections include a second protective projection and a third protective projection that are provided on the second surface, and the nozzle is disposed between the second protective projection and the third protective projection.

In the one aspect of the invention, it is preferable that the second surface has two respectively extending parts extending from both end parts of an outer peripheral part of the second surface, and one of the two extending parts is provided with the second protective projection and the other extending part is provided with the third protective projection.

In the one aspect of the invention, it is preferable that the second and third protective projections and the nozzle have the same height.

In the one aspect of the invention, it is preferable that the second protective projection and the third protective projection are provided to project forward of the nozzle.

In the one aspect of the invention, it is preferable that the plurality of protective projections include a fourth protective projection and a fifth protective projection that are provided on the first surface, and the nozzle is disposed between the fourth protective projection and the fifth protective projection.

In the one aspect of the invention, it is preferable that the fourth and fifth protective projections and the nozzle have the same height.

In the one aspect of the invention, it is preferable that the fourth protective projection and the fifth protective projection are provided to project forward of the nozzle.

In the one aspect of the invention, it is preferable that the plurality of protective projections are disposed outside an endoscope observation range.

In the one aspect of the invention, it is preferable that the plurality of protective projections are disposed outside a visual field range of the observation window.

According to the invention, the contacted member coming into contact with the distal end surface can be prevented from coming into contact with the observation window by the nozzle and the plurality of protective projections provided on the distal end surface of the insertion part. Additionally, by disposing the nozzle or the protective projection such that at least a portion of the nozzle is included within the outer ring region surrounded by the plurality of protective projections, the nozzle also comes into contact with the protective projections in a case where the nozzle comes into contact with the contacted member. Thus, the impact to the nozzle resulting from the contact of the contacted member can be alleviated.

DESCRIPTION OF THE PREFERRED EMBODIMENTS

Hereinafter, preferable embodiments of an endoscope related to the invention will be described according to the accompanying drawings.

Figure 1:
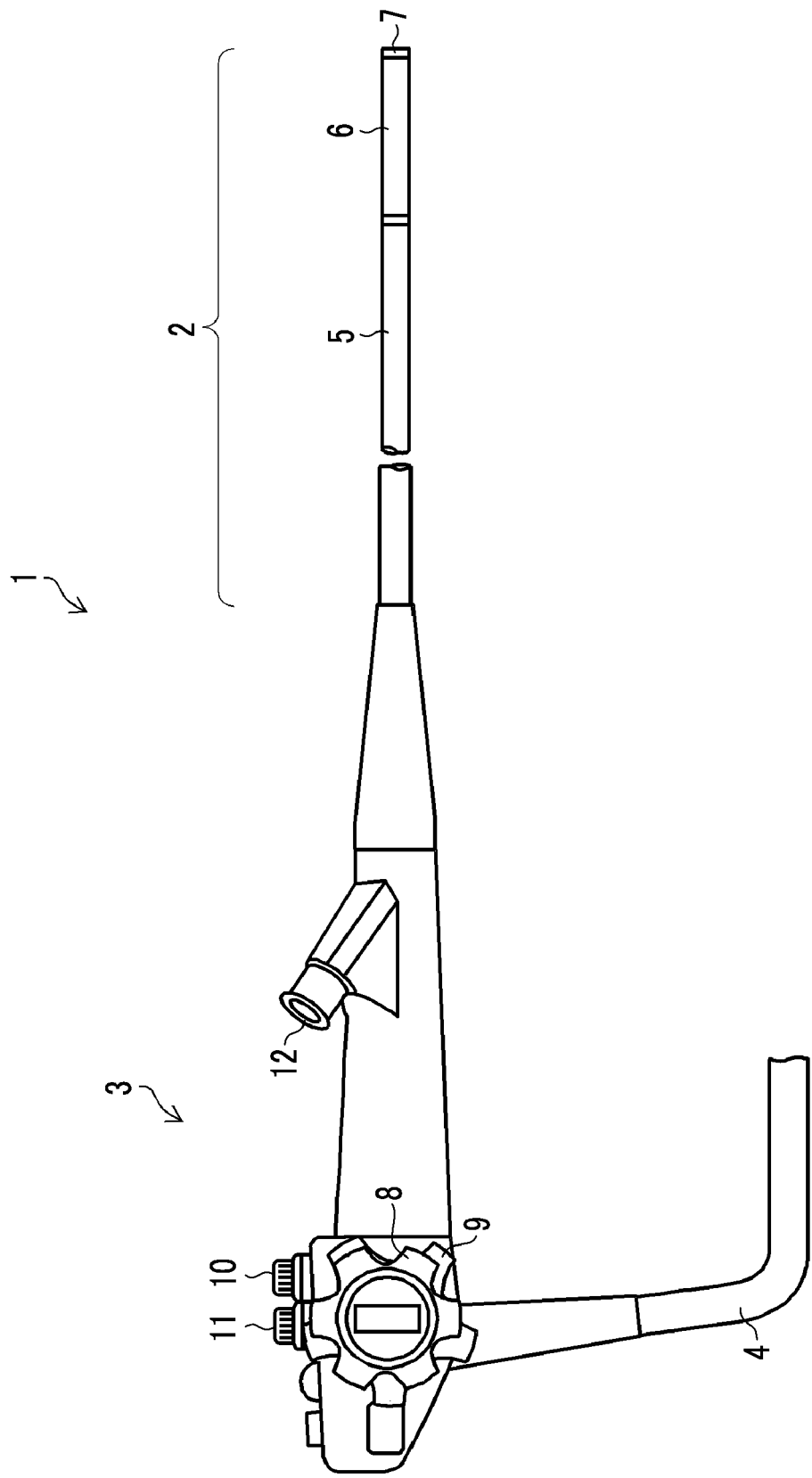
FIG. 1 is an overall view of an endoscope to which the invention is applied.

FIG. 1 is a configuration view illustrating an endoscope 1 related to an embodiment of the invention. An endoscope 1 in this drawing includes an insertion part 2 inserted into a patient's body, an operating part 3 installed consecutively with a proximal end of the insertion part 2 and used for gripping the endoscope 1, operating the insertion part 2, and the like, and a universal cord 4 connected the endoscope 1 to system constituent devices, such as a light source device (not illustrated) and a processor device. In addition, the endoscope 1 of the present embodiment is a lower endoscope (colonoscope) that observes the large intestine or the like.

The insertion part 2 has a distal end, a proximal end, and a longitudinal axis, and is constituted of a flexible part 5, a bending part 6, and a distal end part 7 that are sequentially and consecutively provided from the proximal end toward a distal end. The flexible part 5 has flexibility and bends in random directions along an insertion path of the insertion part 2. The bending part 6 bends in upward, downward, rightward, and leftward directions through the operation of angle knobs 8 and 9 of the operating part 3. The distal end part 7 includes an illumination unit or the like that irradiates an observation unit for imaging an observation area in a living body or an area to be observed with illumination light.

First Embodiment

Figure 2:
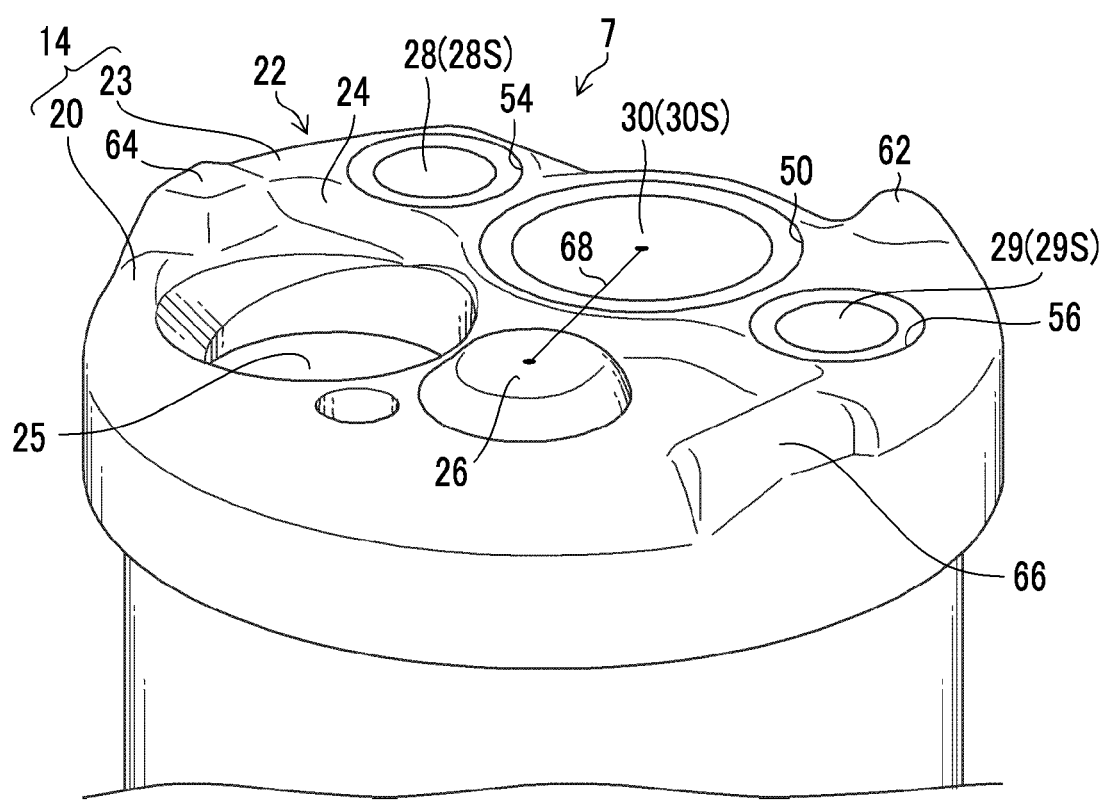
FIG. 2 is a perspective view of a distal end part of a first embodiment.
Figure 3:
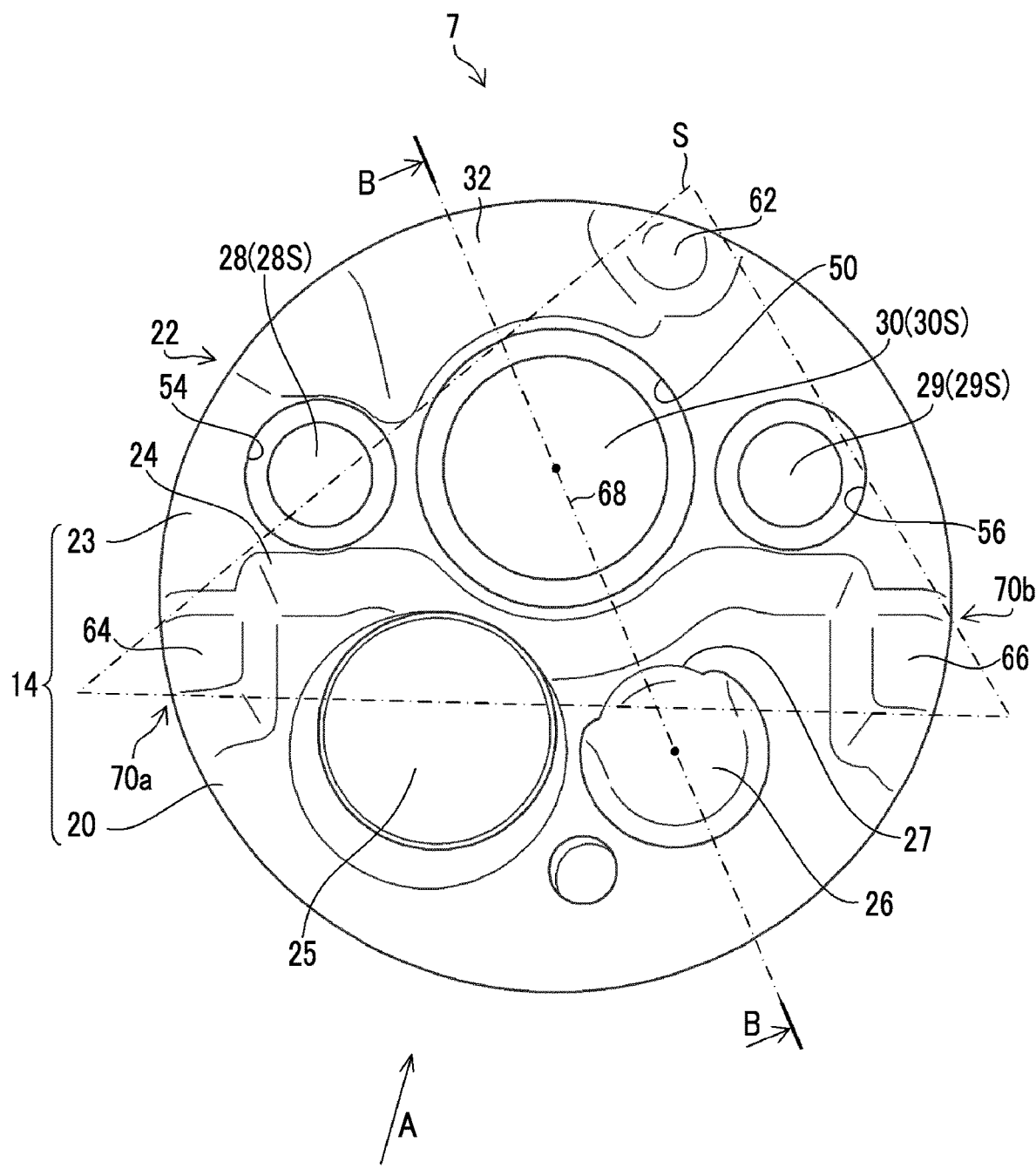
FIG. 3 is a plan view of the distal end part of the first embodiment.

FIG. 2 is an enlarged perspective view illustrating the distal end part 7 of the first embodiment, and FIG. 3 is a plan view. As illustrated in FIGS. 2 and 3, the distal end part 7 has a distal end surface 14 including a first surface 20, and a second surface 23 provided on a projecting part 22 projecting from the first surface 20 forward. The distal end surface 14 is formed on the basis of a circular flat surface centered on an intersection position with the longitudinal axis, a substantial semicircle of the distal end surface 14 becomes the first surface 20, and the remaining region becomes the second surface 23. A boundary portion between the first surface 20 and the second surface 23 is formed by an inclined surface 24 of which the height gradually increases forward from the first surface 20 toward the second surface 23. The first surface 20 has a treatment tool outlet 25 and a fluid jetting nozzle 26, and the like. Additionally, the second surface 23 has a first illumination window 28, a second illumination window 29, an observation window 30, and the like. In addition, in the following, simply the term "longitudinal axis" indicates the longitudinal axis of the insertion part 2. Additionally, the "front side" means a distal end side of the longitudinal axis of the insertion part 2.

The observation window 30 is a constituent element of the observation unit that acquires an image of an area to be observed in order to observe the inside of a subject, and takes subject light from the area to be observed into an optical system (an imaging lens and the like), which is another constituent element of the observation unit, and imaging means. The image captured by the observation unit is sent to the processor device connected by the universal cord 4 as an observation image (endoscopic image).

The first illumination window 28 and the second illumination window 29 are constituent elements of the illumination unit to be mounted on the distal end part 7, and irradiate the area to be observed with illumination light emitted from a light emitting part that is another constituent element of the illumination unit. The illumination light emitted from the light emitting part is propagated through a light guide inserted through the endoscope 1 from the light source device connected by the universal cord 4.

A treatment tool outlet 25 communicates with a treatment tool inlet 12 (refer to FIG. 1) of the operating part 3 through a treatment tool insertion channel inserted through the insertion part 2, and a treatment tool inserted from the treatment tool inlet 12 is delivered from the treatment tool outlet.

Additionally, a suction channel is coupled to the treatment tool insertion channel, and suction from the treatment tool outlet 25 is performed by the operation of a suction button 11 (refer to FIG. 1) of the operating part 3.

The fluid jetting nozzle 26 has a jetting port 27, which is an opening that jets a fluid, disposed toward the observation window 30, and jets a cleaning liquid or gas to a surface 30S of the observation window 30 and a peripheral part thereof.

The fluid jetting nozzle 26 communicates with an air/water supply channel inserted through the endoscope 1, and is connected to an air/water supply device (not illustrated) connected to the universal cord 4, via the air/water supply channel.

Then, in a case where a leakage hole formed in an air/water supply button 10 (refer to FIG. 1) of the operating part 3 is closed by a finger, the gas from the air/water supply device is jetted from the fluid jetting nozzle 26, and in a case where the air/water supply button 10 is pushed with the finger that has closed the leakage hole, the cleaning liquid from the air/water supply device is jetted from the fluid jetting nozzle 26.

In addition, as a procedure of cleaning the observation window 30, for example, after the cleaning liquid is jetted from the fluid jetting nozzle 26 to remove adhering substances, such as blood and a body fluid, which have adhered to the observation window 30, the gas is jetted from the fluid jetting nozzle 26 to remove the cleaning liquid remaining on the observation window 30 or a region adjacent thereto.

Here, a planar arrangement relationship of the respective parts on the distal end surface 14 will be described with reference to FIG. 3. As described above, the observation window 30, the first illumination window 28, and the second illumination window 29 are disposed on the second surface 23. Specifically, the observation window 30 is provided at a position biased to a peripheral edge of the distal end surface with respect to the center of the distal end surface 14. The first illumination window 28 is provided on one side of the observation window 30, and the second illumination window 29 is provided on a side opposite to the first illumination window 28 across the observation window 30. Additionally, the fluid jetting nozzle 26 and the treatment tool outlet 25 are disposed on the first surface 20. Specifically, the fluid jetting nozzle 26 is provided at a position where the jetting port 27 faces the observation window 30. The treatment tool outlet 25 is disposed at a position adjacent to the fluid jetting nozzle 26.

A surface 30S of the observation window 30 is constituted of a convex surface projecting toward the front side, and is disposed in an opening 50 formed in the projecting part 22. In addition, a gap between a peripheral edge of the surface 30S of the observation window 30 and a peripheral edge of the opening 50 is sealed and fixed with an adhesive 52, and a surface 52S (refer to FIG. 4) of the adhesive 52 is disposed between the peripheral edge of the surface 30S of the observation window 30 and the peripheral edge of the opening 50.

A surface 28S of the first illumination window 28 and a surface 29S of the second illumination window 29 are respectively disposed perpendicularly to the longitudinal axis of the insertion part 2, and are respectively disposed in openings 54 and 56 formed in the second surface 23. Also regarding the first illumination window 28 and the second illumination window 29, a gap between a peripheral edge of the surface 28S of the first illumination window 28 and a peripheral edge of an opening 54 and a gap between the peripheral edge of the surface 29S of the second illumination window 29 and a peripheral edge of an opening 56 are sealed and fixed with adhesives.

Figure 4:
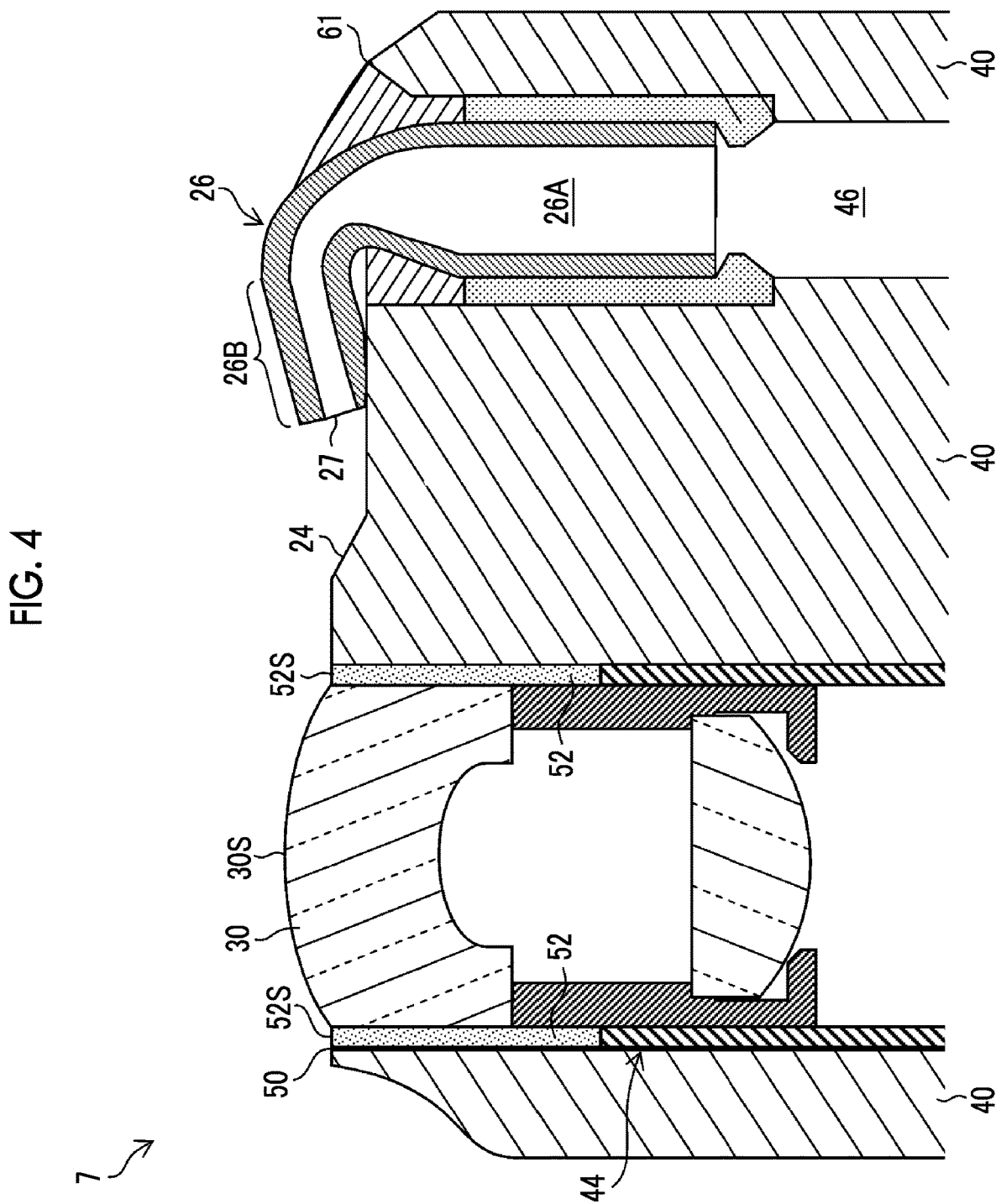
FIG. 4 is a cross-sectional view taken along arrow B-B of the distal end part of FIG. 3.

FIG. 4 is a cross-sectional view as seen in the direction of arrow B-B of FIG. 3. The distal end part 7 is formed of hard materials, such as metal, and has the distal end part body 40 that holds various components disposed in the distal end part 7.

In addition, in this drawing, a lens barrel 44 that accommodates the observation window 30 and an imaging lens that constitute the observation unit, and an end part of the air/water supply channel 46 connected to the fluid jetting nozzle 26 are illustrated as components held by the distal end part body 40. An optical axis of the observation window 30 (and imaging lens) is substantially parallel to the longitudinal axis of the insertion part 2 in the present embodiment.

The fluid jetting nozzle 26 is disposed such that the shape thereof from a proximal end portion 26A connected to the end part of the air/water supply channel 46 as illustrated in FIG. 4 to a distal end portion 26B in which the jetting port 27 is formed is L-shaped, and the distal end portion 26B of the fluid jetting nozzle 26 projects from an opening 61 formed in the distal end part body 40 to the distal end side in the direction of the longitudinal axis of the insertion part 2.

Additionally, the jetting port 27 of the fluid jetting nozzle 26 is an oblong opening (plane) substantially perpendicular to an axis of a pipe line of the fluid jetting nozzle 26, and is disposed such that a jetting axis passing through the center of the jetting port 27 faces substantially the center of the surface 30S of the observation window 30 in a front view of the distal end surface 14 as seen from the direction of the longitudinal axis of the insertion part 2. In addition, an adhesive (not illustrated) is disposed between an outer wall surface of the fluid jetting nozzle 26 and a peripheral edge of an opening 61.

A fluid discharge surface 32, which is inclined rearward as the distance from the observation window 30 increases, is provided on the side opposite to the fluid jetting nozzle 26 with respect to the observation window 30 of the second surface 23. The cleaning liquid jetted from the fluid jetting nozzle 26 is discharged from the fluid discharge surface 32 after passing through the observation window 30.

A plurality of protective projections projecting forward of the observation window 30 are provided at an outer peripheral part of the distal end surface 14. In FIGS. 2 and 3, three protective projections of a first protective projection 62, a second protective projection 64, and a third protective projection 66 are provided on the distal end surface 14. By combining the first protective projection 62, the second protective projection 64 and the third protective projection 66, and the fluid jetting nozzle 26 together, a contacted member in front of the distal end surface 14 can be prevented from coming into contact with the observation window 30.

The first protective projection 62 is provided on the second surface 23, and is disposed at a position offset to one side of an imaginary straight line 68 connecting the center of the fluid jetting nozzle 26 and the center of the observation window 30 together. The second protective projection 64 and the third protective projection 66 are disposed at two extending parts 70a and 70b extending along an outer peripheral part of the first surface 20 from both end parts of an outer peripheral part of the second surface 23. The second protective projection 64 is provided on one extending part 70a out of the extending parts 70a and 70b, and the third protective projection 66 is provided on the other extending part 70b out of the extending parts 70a and 70b.

Additionally, a positional relationship among the first protective projection 62, the second protective projection 64 and the third protective projection 66, and the observation window 30 is such that, as illustrated in FIG. 3 in plan view of the distal end surface 14 of the distal end part 7 as seen from the direction of the longitudinal axis of the insertion part 2, the entire region of the observation window 30 is included within an outer ring region S surrounded by the first protective projection 62, the second protective projection 64, and the third protective projection 66. In addition, the "outer ring region" indicates an outer profile region defined by the outer profiles of the first protective projection 62, the second protective projection 64, and the third protective projection 66 in a case where the distal end surface 14 is seen from the front side, that is, in a case where the first protective projection 62, the second protective projection 64, the third protective projection 66, and the nozzle are projected on a projection plane parallel to the distal end surface 14. In FIG. 3, since the three protective projections are provided, the outer ring region S has a triangular shape. However, in a case where four or more protective projections are provided, the outer ring region S has a polygonal shape in which apexes or sides adjacent protective projections are connected together.

Additionally, the positional relationship among the first protective projection 62, the second protective projection 64 and the third protective projection 66, and the fluid jetting nozzle 26 is such that a portion of the fluid jetting nozzle 26 is included within the outer ring region S in plan view of the distal end surface 14 as seen from the direction of the longitudinal axis.

The observation window 30 is disposed at a position included within the outer ring region S. In addition, in all combinations of imaginary planes capable of coming into contact with the first protective projection 62, the second protective projection 64, the third protective projection 66, and the fluid jetting nozzle 26 from the front side, the imaginary planes are set so as to be disposed forward of the observation window 30.

An imaginary plane coming into contact with the first protective projection 62, the second protective projection 64, and the third protective projection 66 is supposed as an imaginary plane coming into contact with the first protective projection 62, the second protective projection 64, and the third protective projection 66 from the front side, and the height of the first protective projection 62, the second protective projection 64, and the third protective projection 66 and the positions thereof on the distal end surface 14 are determined such that the imaginary plane is disposed on the front side with respect to the observation window 30. By setting the imaginary plane so as to be disposed on the front side with respect to the observation window 30, the contacted member coming into contact from the front side can be prevented from coming into contact with the observation window 30 by coming into contact with the first protective projection 62, the second protective projection 64, and the third protective projection 66. Hence, the observation window 30 can be protected.

Figure 5:
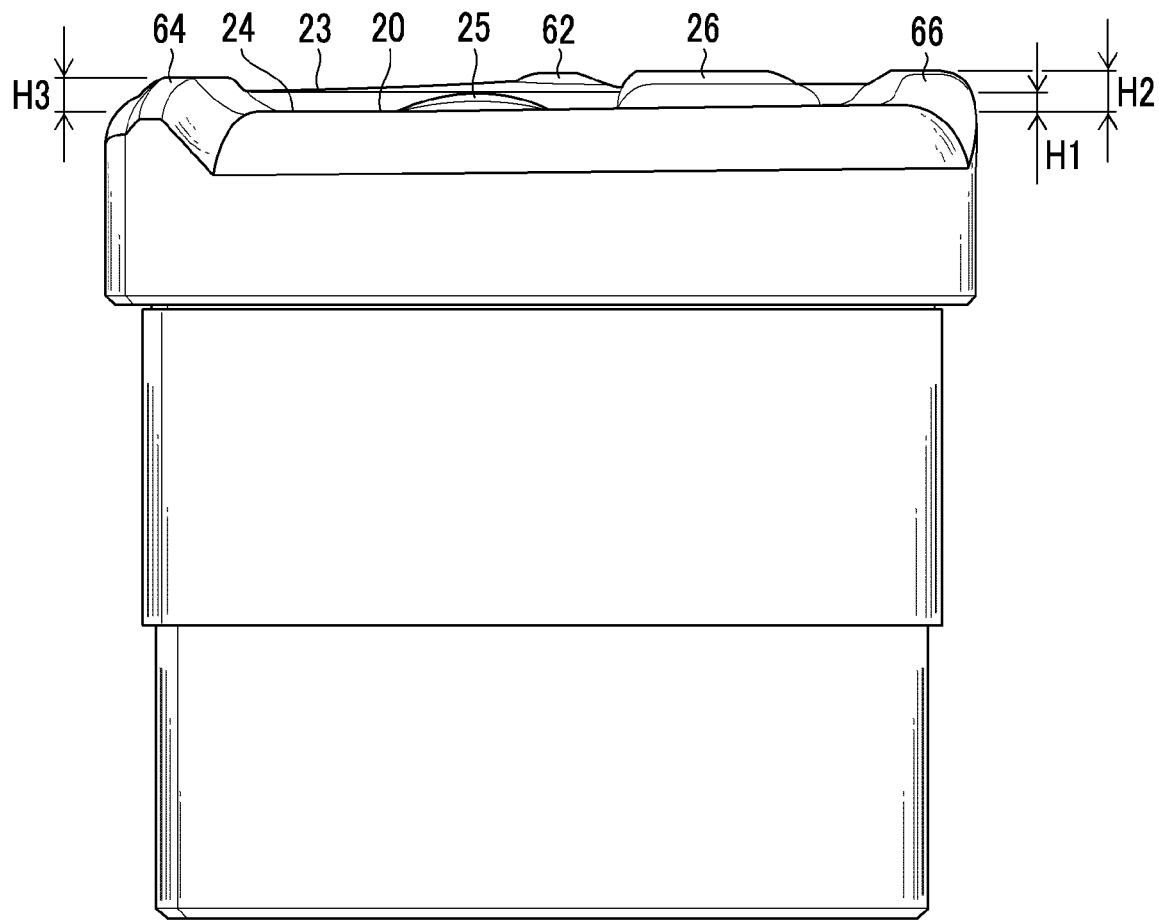
FIG. 5 is a side view of the distal end part of FIG. 3 as seen from arrow A.

FIG. 5 is a view as seen from arrow A in FIG. 3. A positional relationship of the distal end surface 14 of in a longitudinal direction will be described with reference to FIG. 5.

In a case where the first surface 20 is used as a reference surface, a height from the first surface 20 to the second surface 23 is defined as H1. A height from the first surface 20 to the first protective projection 62, the second protective projection 64, and the third protective projection 66 is defined as H2. A height from the first surface 20 to the fluid jetting nozzle 26 is defined as H3.

The second surface 23 is provided to project forward of the first surface 20. The observation window 30 is disposed on the second surface 23, and the fluid jetting nozzle 26 is disposed on the first surface 20. By providing the observation window 30 on the second surface 23 and providing the fluid jetting nozzle 26 on the first surface 20, the height of a topmost part of the fluid jetting nozzle 26 with respect to the observation window 30 can be made low. Hence, the fluid jetting nozzle 26 can be prevented from entering a visual field range of the observation window 30, and the visual field range of the observation window 30 can be secured.

As described above, the first surface 20 and the second surface 23 are connected together by the inclined surface 24. By forming the inclined surface 24 between the first surface 20 and the second surface 23, the cleaning liquid jetted from the fluid jetting nozzle 26 can be easily supplied to the observation window 30.

Additionally, the height H2 of the second protective projection 64 and the third protective projection 66 from the first surface 20 is the same as the height H3 of the fluid jetting nozzle 26 from the first surface 20. By making the height of the second protective projection 64 and the third protective projection 66, and the height of the fluid jetting nozzle 26 equal to each other, the contacted member coming into contact from the front side comes into contact with the fluid jetting nozzle 26 and comes into contact with at least one of the second protective projection 64 and the third protective projection 66. Therefore, the impact of the contacted member against the fluid jetting nozzle 26 can be suppressed. Hence, damage and peeling of the fluid jetting nozzle 26 can be suppressed.

In addition, in FIG. 3, although the height H2 and the height H3 are made to be the same height, a configuration in which the height H2 is increased and the second protective projection 64 and the third protective projection 66 project forward of the fluid jetting nozzle 26 may be adopted. By disposing the second protective projection 64 and the third protective projection 66 forward of the fluid jetting nozzle 26, the contact of the fluid jetting nozzle 26 with the contacted member after the second protective projection 64 and the third protective projection 66 come into contact with the contacted member coming into contact from the front side, or the contact of the fluid jetting nozzle 26 with the contacted member can be prevented, and damage and peeling of the fluid jetting nozzle 26 can be prevented.

Referring to FIGS. 2 and 3, an arrangement relationship among the first protective projection 62, the second protective projection 64, and the third protective projection 66 on the distal end surface 14 will be further described.

As described above, the first protective projection 62 is disposed at a position offset to one side of the imaginary straight line 68 connecting the center of the fluid jetting nozzle 26 and the center of the observation window 30 together. The cleaning liquid jetted from the fluid jetting nozzle 26 passes through the observation window 30, and is discharged from the fluid discharge surface 32. By shifting and disposing the first protective projection 62 from a position different from the fluid discharge surface 32, that is, from the side opposite to the fluid jetting nozzle 26 with respect to the observation window 30, the cleaning liquid can be discharged without the cleaning liquid remaining on the distal end surface 14. Additionally, in plan view of the distal end surface 14 as seen from the direction of the longitudinal axis, a gap between the observation window 30 and the contacted member in a case where the contacted member has come into contact with the first protective projection 62 can be widen by increasing the spacing between the first protective projection 62 and the observation window 30.

It is preferable that the second protective projection 64 and the third protective projection 66 are disposed apart from the first illumination window 28 and the second illumination window 29. By disposing the second protective projection 64 and the third protective projection 66 apart from the first illumination window 28 and the second illumination window 29, the cleaning liquid jetted from the fluid jetting nozzle 26 can be prevented from remaining in the vicinity of the second protective projection 64 and the third protective projection 66, and adhesion of dirt to the first illumination window 28 and the second illumination window 29 due to water droplets or residues can be prevented. In the first embodiment, the extending parts 70a and 70b are provided, and the second protective projection 64 and the third protective projection 66 are provided. Additionally, the first illumination window 28 and the second illumination window 29 are sealed and fixed to the distal end part body 40 with an adhesive. By disposing the second protective projection 64 and the third protective projection 66 apart from the first illumination window 28 and the second illumination window 29, coating work of the adhesive in a case where the first illumination window 28 and the second illumination window 29 are sealed and fixed to the distal end part body 40 can be easily performed.

In the present embodiment, by projecting the first protective projection 62, the second protective projection 64, and the third protective projection 66 forward, the contacted member can be prevented from coming into contact with the observation window 30. Additionally, the impact resulting from the contact of the contacted member with the fluid jetting nozzle 26 can be suppressed. In a case where the height of the first protective projection 62, the second protective projection 64, and the third protective projection 66 is increased, the first protective projection 62, there is a case where the second protective projection 64, and the third protective projection 66 may be reflected within an endoscope observation range to be observed by the observation window 30. Particularly, in the lower endoscope like the endoscope of the present embodiment, a visual field range of about 170° is obtained in order to widen the range of a subject observable from the observation window 30. For that reason, it is preferable that the first protective projection 62, the second protective projection 64, and the third protective projection 66 are provided on the distal end surface 14 outside the endoscope observation range. The endoscope observation range is an image range within a monitor in a case where an observation image captured by the observation unit is output to the monitor (not illustrated) connected to the processor device. Moreover, it is preferable that the first protective projection 62 and the second protective projection 64 is disposed outside the visual field range of the observation window 30. The visual field range of the observation window 30 means a visual field range taken in via an optical system of the observation unit. In order to dispose the first protective projection 62, the second protective projection 64, and the third protective projection 66 outside the endoscope observation range, the disposition can be performed by setting the height of the first protective projection 62, the second protective projection 64, and the third protective projection 66 and the positions thereof within the distal end surface 14.

Modification Examples

Figure 6:
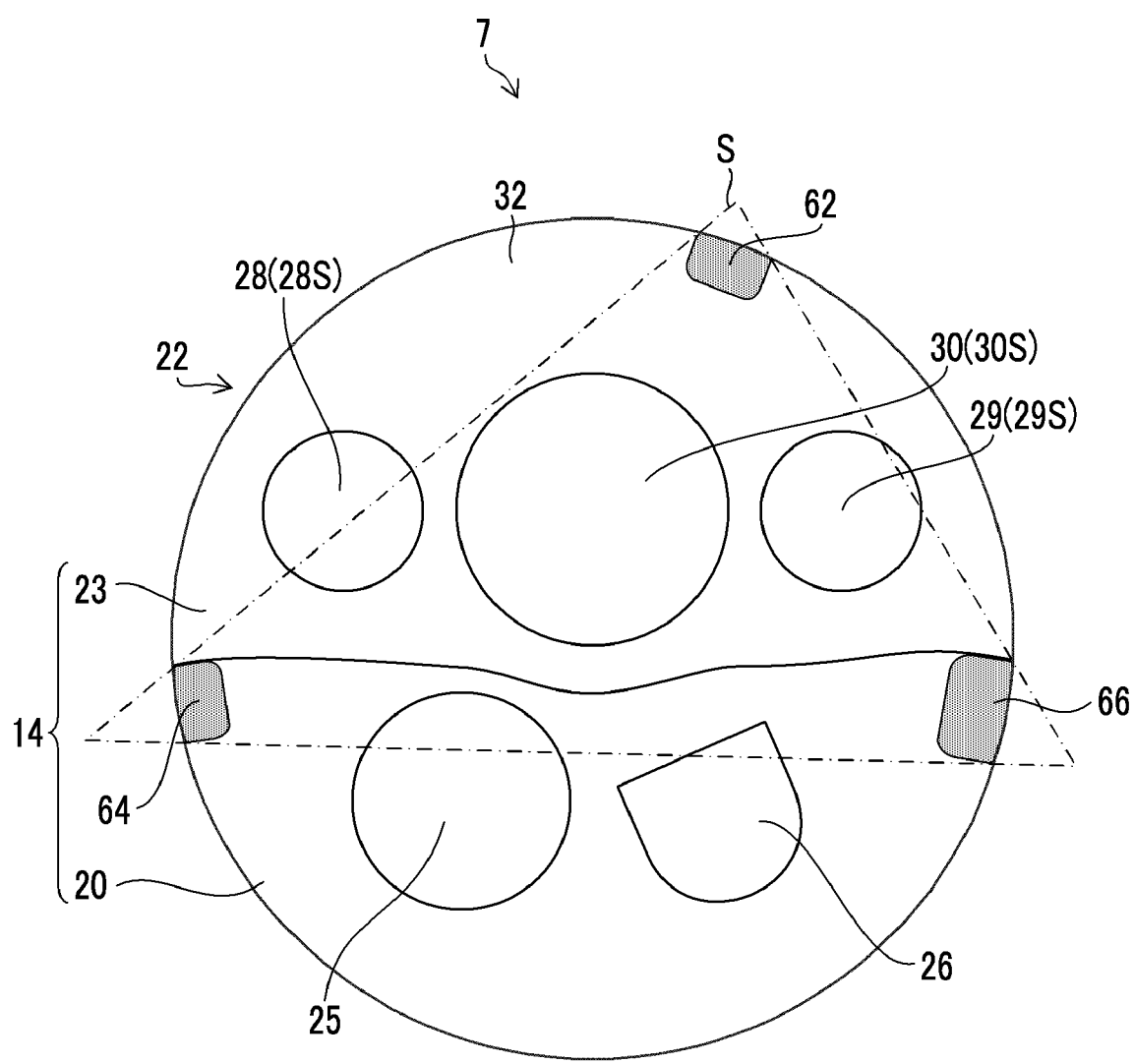
FIG. 6 is a simplified diagram of the distal end part of the first embodiment.
Figure 7:
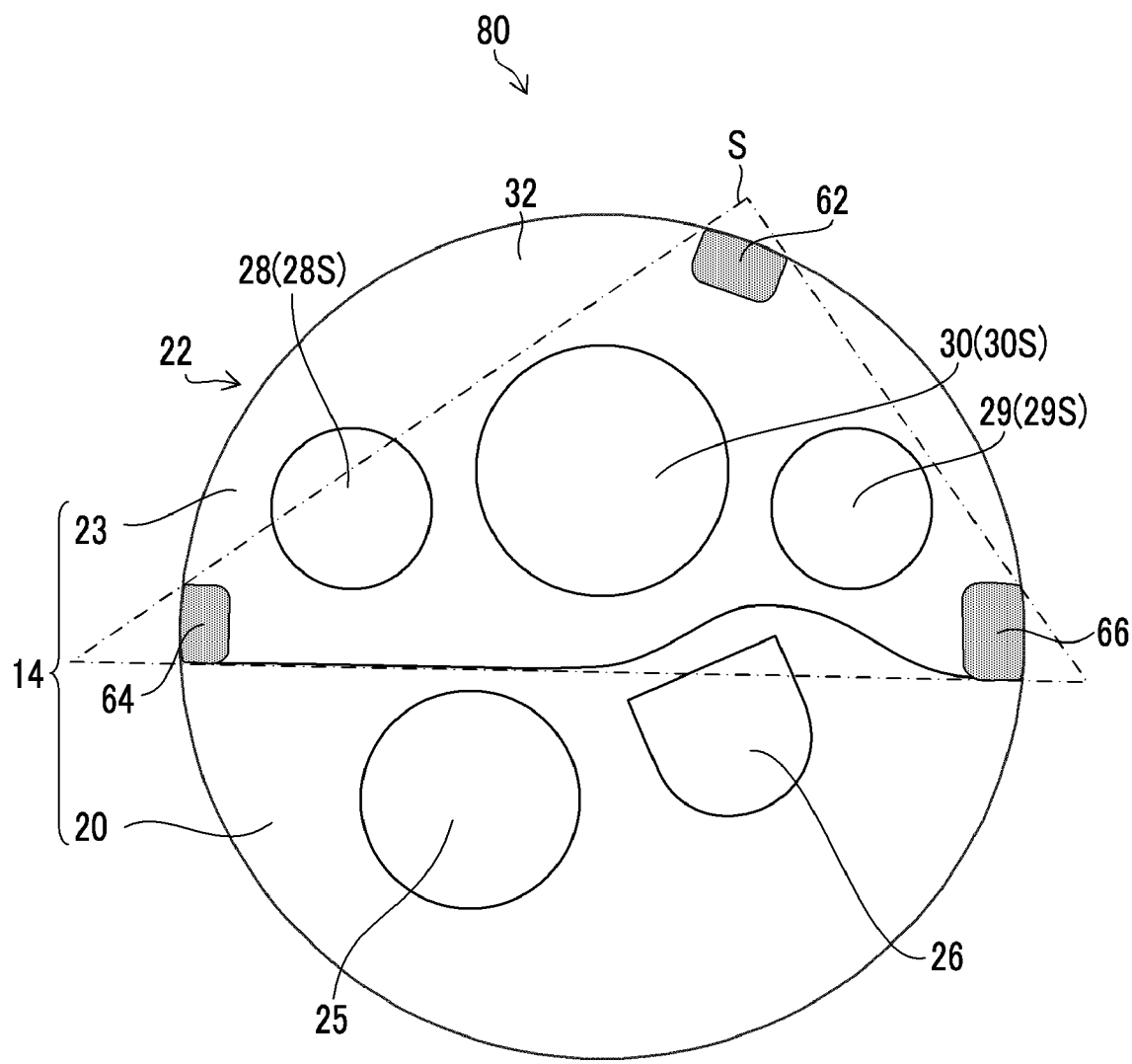
FIG. 7 is a simplified diagram of a distal end part illustrating a modification example of the first embodiment.

Next, modification examples of the distal end surface of the first embodiment will be described in simplified diagrams of the distal end surface. FIG. 6 is a simplified diagram of the first embodiment illustrating in FIG. 3, and FIG. 7 is a simplified diagram of a distal end part 80 of a modification example of the first embodiment. Although the distal end part 80 illustrated in FIG. 7 has the second protective projection 64 and the third protective projection 66 on the second surface 23, the distal end part 80 is different from the distal end part 7 in that the extending parts illustrated in FIG. 6 are not provided.

In the distal end part 80 illustrated in FIG. 7, the second protective projection 64 and the third protective projection 66 are provided on the second surface 23 without providing the extending parts, and the observation window 30 is included within the outer ring region S surrounded by the first protective projection 62, the second protective projection 64, and the third protective projection 66. Additionally, the fluid jetting nozzle 26 is disposed between the second protective projection 64 and the third protective projection 66, and at least a portion of the fluid jetting nozzle 26 is included within the outer ring region S. Accordingly, the contact of the contacted member with the observation window 30 can be prevented. Additionally, the impact of the contacted member against the fluid jetting nozzle 26 can be reduced.

Figure 8:
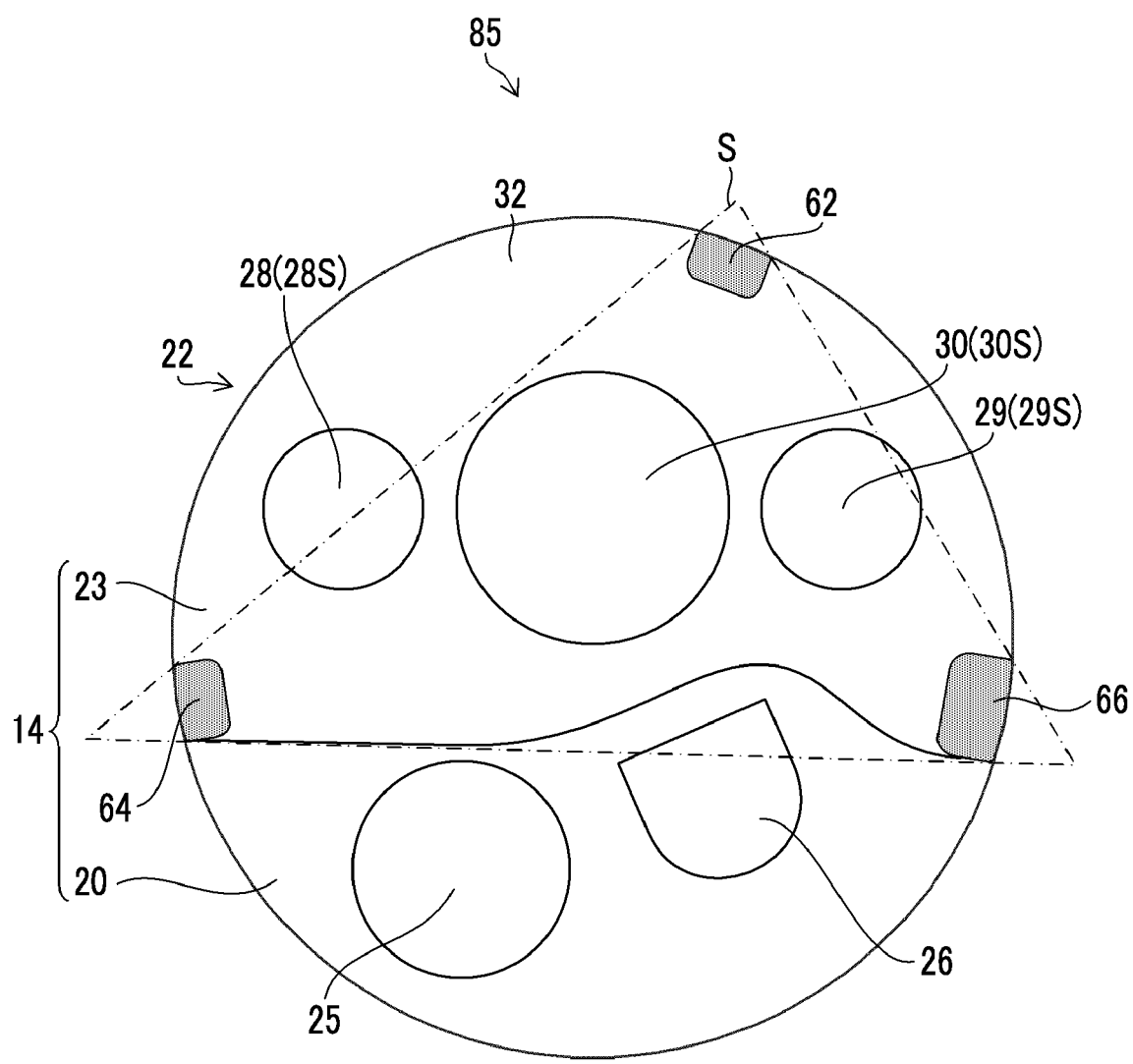
FIG. 8 is a simplified diagram of a distal end part illustrating another modification example of the first embodiment.

FIG. 8 is a simplified diagram of a distal end part 85 illustrating another modification example. The distal end part 85 illustrated in FIG. 8 is formed such that the second surface 23 is wider toward the first surface 20 side than the distal end part 7 illustrated in FIG. 6. The second protective projection 64 and the third protective projection 66 are disposed at an outer edge part of the distal end surface 14 in the boundary portion between the second surface 23 and the first surface 20. By setting the boundary portion between the second surface 23 and the first surface 20 on the observation window 30 side in a central portion of the distal end surface 14, the fluid jetting nozzle 26 provided on the first surface 20 can be disposed between the second protective projection 64 and the third protective projection 66. By providing the fluid jetting nozzle 26 between the second protective projection 64 and the third protective projection 66, a portion of the fluid jetting nozzle 26 can be included within the outer ring region S of the first protective projection 62, the second protective projection 64, and the third protective projection 66.

It is preferable that the positions of the second protective projection 64 and the third protective projection 66 are disposed apart from the first illumination window 28 and the second illumination window 29, as in the first embodiment.

Second Embodiment

Figure 9:
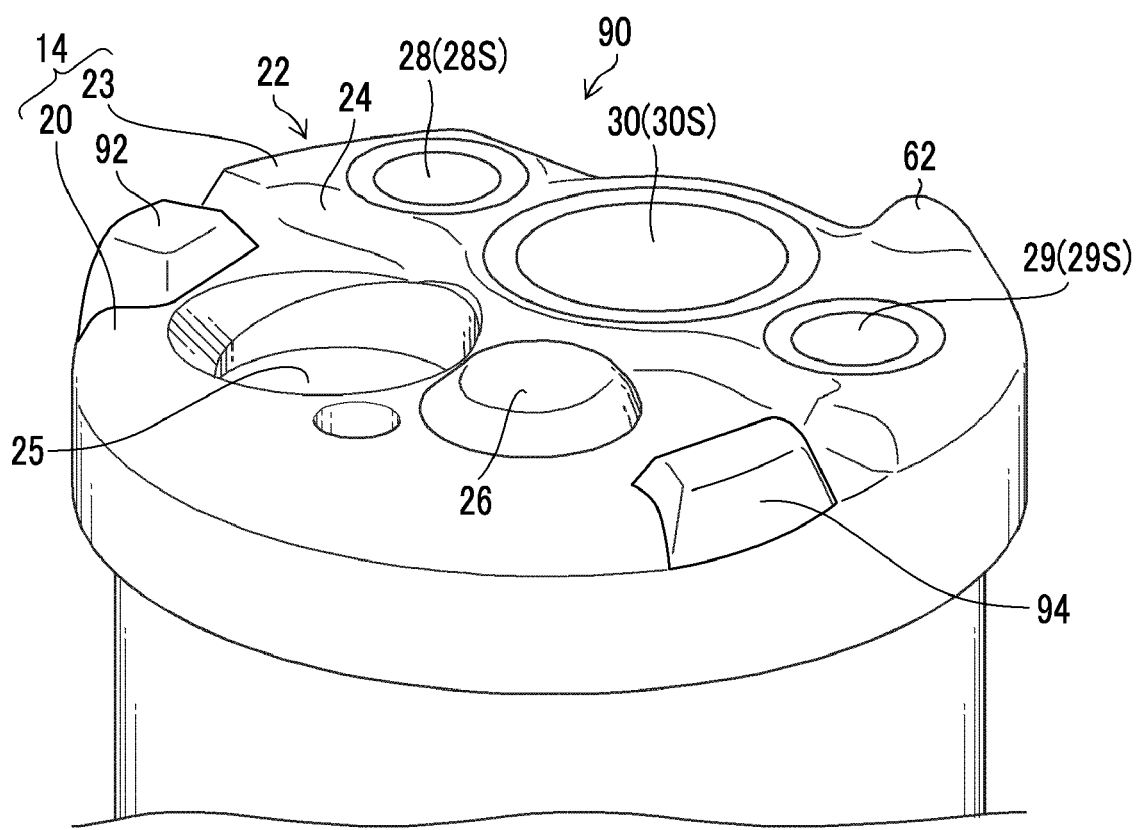
FIG. 9 is a perspective view of a distal end part of a second embodiment.
Figure 10:
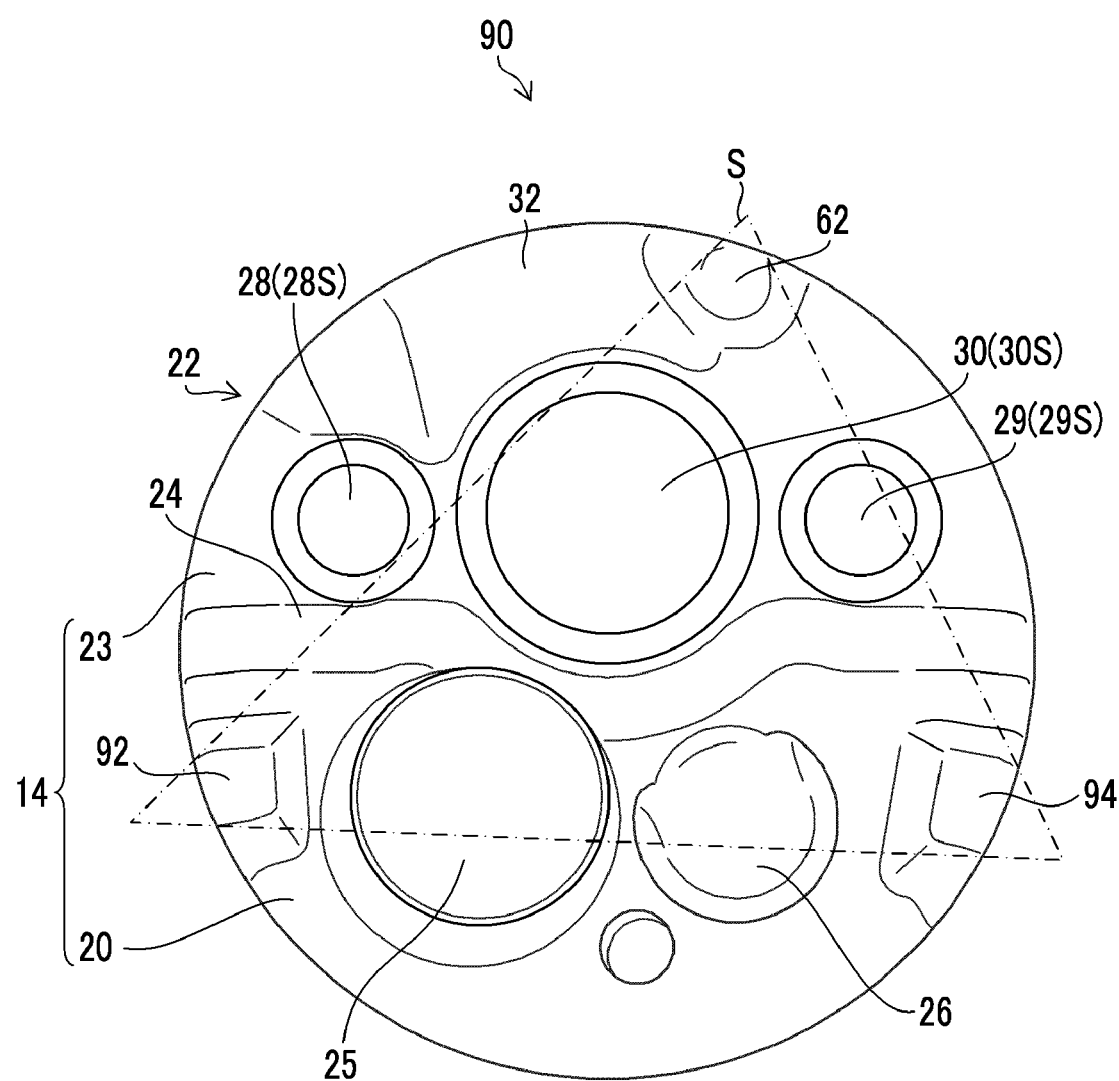
FIG. 10 is a plan view of the distal end part of the second embodiment.

FIG. 9 is an enlarged perspective view illustrating a distal end part 90 of a second embodiment, and FIG. 10 is a plan view. The distal end part 90 illustrated in FIGS. 9 and 10 is different from the distal end part 7 illustrated in the first embodiment in that a fourth protective projection 92 and a fifth protective projection 94 are provided on the first surface 20.

The second embodiment is the same as the first embodiment in that the first surface 20 and the second surface 23 are provided, the treatment tool outlet 25 and the fluid jetting nozzle 26 are provided on the first surface 20, and the first illumination window 28, the second illumination window 29, and the observation window 30 are provided on the second surface 23.

In the second embodiment, the fourth protective projection 92 and the fifth protective projection 94 are provided on the first surface 20. Similar to the second protective projection and the third protective projection of the first embodiment, the height of the fourth protective projection 92 and the fifth protective projection 94 is made higher than or made equal to the height of the fluid jetting nozzle 26. Moreover, portions of the observation window 30 and fluid jetting nozzle 26 are disposed so as to be included within the outer ring region S surrounded by the first protective projection 62, the fourth protective projection 92, and the fifth protective projection 94. Accordingly, the contact of the contacted member with the observation window 30 can be prevented, and the impact of the contacted member with the fluid jetting nozzle 26 can be reduced.

Regarding a positional relationship among the fourth protective projection 92 and the fifth protective projection 94, and the fluid jetting nozzle 26 in the direction of the longitudinal axis of the insertion part 2, the height of the fourth protective projection 92 and the fifth protective projection 94 from the first surface 20 and the height from the first surface 20 of the fluid jetting nozzle 26 are set to the same height. Accordingly, since the contacted member coming into contact from the front side does not come into contact with the fourth protective projection 92 and the fifth protective projection 94 and the contacted member does not come into contact with the fluid jetting nozzle 26 directly, the impact from the contacted member o the fluid jetting nozzle 26 can be suppressed. Otherwise, the height of the fourth protective projection 92 and the fifth protective projection 94 from the first surface 20 can be made higher than the height from the first surface 20 of the fluid jetting nozzle 26. Accordingly, since the contacted member and the fluid jetting nozzle 26 do not come into contact with each other or the fluid jetting nozzle 26 comes into contact with the contacted member after the fourth protective projection 92 or the fifth protective projection 94 come into contact with the contacted member even in a case where the contacted member and the fluid jetting nozzle 26 come into contact with each other, the impact from the contacted member can be suppressed. Hence, damage and peeling of the fluid jetting nozzle 26 can be suppressed.

By providing the fourth protective projection 92 and the fifth protective projection 94 on the first surface 20, the area of the outer ring region S can be increased as compared to the first embodiment. Hence, in plan view in the direction of the longitudinal axis of the insertion part 2, most of the fluid jetting nozzle 26 can be included within the outer ring region S. Thus, the impact of the contacted member to the fluid jetting nozzle 26 can be reduced.

Additionally, by providing the fourth protective projection 92 and the fifth protective projection 94 on the first surface 20, as compared to the case of the first embodiment, the distance from the observation window 30 to the fourth protective projection 92 and the distance from the observation window 30 to the fifth protective projection 94 can be lengthened in plan view in the direction of the longitudinal axis. Hence, even in a case where the height from the first surface 20 of the fourth protective projection 92 and the fifth protective projection 94 is made higher than the height from the first surface 20 of the second protective projection 64 and the third protective projection 66 of the first embodiment, the fourth protective projection 92 and the fifth protective projection 94 can be prevented being reflected within the endoscope observation range to be observed by the observation window 30. By making the height of the fourth protective projection 92 and the fifth protective projection 94 from the first surface 20 high, the contact of the contacted member with the observation window 30 and the contact contacted member with the fluid jetting nozzle 26 can be prevented.

In addition, in the first embodiment and the second embodiment, an aspect in which the three protective projections are provided has been described. However, the number of protective projections is not particularly limited. In a case where four or more protective projections are provided. The effects of the invention can be exhibited by disposing the observation window and a portion of the fluid jetting nozzle so as to be included within an outer ring region surrounded by all the protective projections.

EXPLANATION OF REFERENCES

1: endoscope
2: insertion part
3: operating part
4: universal cord
5: flexible part
6: bending part
7, 80, 85, 90: distal end part
8, 9: angle knob
10: air/water supply button
11: suction button
12: treatment tool inlet
14: distal end surface
20: first surface
22: projecting part
23: second surface
24: inclined surface
25: treatment tool outlet
26: fluid jetting nozzle
26A: proximal end portion
26B: distal end portion
27: jetting port
28: first illumination window
28S, 29S, 30S, 52S: surface
29: second illumination window
30: observation window
32: fluid discharge surface
40: distal end part body
44: barrel
46: air/water supply channel
50, 54, 56, 61: opening
52: adhesive
62: first protective projection
64: second protective projection
66: third protective projection
68: imaginary straight line
70a, 70b: extending part
92: fourth protective projection
94: fifth protective projection
S: outer ring region

What is claimed is:
1. An endoscope comprising:
an insertion part to be inserted into a subject;
a distal end surface provided at a distal end of the insertion part;

an observation window provided on the distal end surface to observe an interior of the subject;

a nozzle provided on the distal end surface to jet a fluid toward the observation window; and a plurality of protective projections disposed at an outer peripheral part of the distal end surface and provided to project forward of the observation window, wherein the plurality of protective projections have a same height as the nozzle or are projected forward of the nozzle, wherein the observation window and at least a portion of the nozzle are included within an outer ring region surrounded by the plurality of protective projections, in plan view of the distal end surface, wherein the distal end surface has a first surface on which the nozzle is disposed and a second surface which is provided at a projecting part projecting forward from the first surface and on which the observation window is disposed, wherein the plurality of protective projections include a first protective projection, a second protective projection, and a third protective projection, and the second and third protective projections are provided on the first surface, wherein the nozzle is disposed between the second protective projection and the third protective projection, wherein the distal end surface has a fluid discharge surface that is provided on a side opposite to the nozzle with respect to the observation window and is inclined rearward as a distance from the observation window increases, wherein the first protective projection is provided at a position adjacent to the fluid discharge surface, and wherein the first protective projection is provided on the second surface, and is disposed at a position offset to one side of an imaginary straight line connecting a center of the nozzle and a center of the observation window.

2. The endoscope according to claim 1, wherein the second and third protective projections and the nozzle have the same height.

3. The endoscope according to claim 1, wherein the second and third protective projections are provided to project forward of the nozzle.

4. The endoscope according to claim 1, wherein the plurality of protective projections are disposed outside an endoscope observation visual field range.

5. The endoscope according to claim 4, wherein the plurality of protective projections are disposed outside a visual field range of the observation window.

* * * * *